United States Patent
Viola

(10) Patent No.: US 9,510,831 B2
(45) Date of Patent: *Dec. 6, 2016

(54) MAGNETIC COMPRESSION ANASTOMOSIS DEVICE

(71) Applicant: Covidien LP, Mansfield, MA (US)

(72) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/481,966

(22) Filed: Sep. 10, 2014

(65) Prior Publication Data

US 2014/0379011 A1 Dec. 25, 2014

Related U.S. Application Data

(63) Continuation of application No. 14/175,353, filed on Feb. 7, 2014, now Pat. No. 8,920,446, which is a continuation of application No. 12/486,846, filed on Jun. 18, 2009, now Pat. No. 8,685,046.

(60) Provisional application No. 61/086,340, filed on Aug. 5, 2008.

(51) Int. Cl.
*A61B 17/08* (2006.01)
*A61B 17/11* (2006.01)
*A61B 17/00* (2006.01)

(52) U.S. Cl.
CPC ...... *A61B 17/11* (2013.01); *A61B 2017/00876* (2013.01); *A61B 2017/111* (2013.01); *A61B 2017/1135* (2013.01)

(58) Field of Classification Search
CPC ............ A61B 17/11; A61B 2017/00876; A61B 2017/111; A61B 2017/1135; A61B 17/115; A61B 17/32053; A61B 2017/1139; A61B 17/32075; A61B 2017/1132
USPC ............................. 606/151, 153; 227/180.1
See application file for complete search history.

(56) References Cited

U.S. PATENT DOCUMENTS

| | | | |
|---|---|---|---|
| 3,986,493 A | 10/1976 | Hendren, III | |
| 4,338,937 A | 7/1982 | Lerman | |
| 4,765,332 A | 8/1988 | Fischell et al. | |
| 4,917,114 A | 4/1990 | Green et al. | |
| 5,250,058 A * | 10/1993 | Miller | A61B 17/11 24/615 |

(Continued)

FOREIGN PATENT DOCUMENTS

| | | |
|---|---|---|
| EP | 0517488 A1 | 12/1992 |
| EP | 0595094 A2 | 5/1994 |

(Continued)

OTHER PUBLICATIONS

English machine translation from EPO for FR 2 760 627 by Pozzi et al.

(Continued)

*Primary Examiner* — Katherine M Shi

(57) ABSTRACT

An apparatus for joining organ wall portions of first and second hollow organs, including first and second connectors, wherein the first and second connectors are magnetically attracted to one another. A device for delivering and deploying the first and second connectors to portions of the first and second hollow organs can be provided, wherein the device is configured and dimensioned to axially align the first and second connectors for performing circular anastomosis of the first and second hollow organs.

13 Claims, 10 Drawing Sheets

(56) References Cited

U.S. PATENT DOCUMENTS

| | | |
|---|---|---|
| 5,342,393 A | 8/1994 | Stack |
| 5,690,656 A | 11/1997 | Cope et al. |
| 6,050,472 A | 4/2000 | Shibata |
| 6,068,637 A | 5/2000 | Popov et al. |
| 6,352,543 B1 | 3/2002 | Cole |
| 6,632,229 B1 | 10/2003 | Yamanouchi |
| 6,719,768 B1 | 4/2004 | Cole et al. |
| 8,685,046 B2 | 4/2014 | Viola |
| 2002/0082625 A1 | 6/2002 | Huxel et al. |
| 2002/0143347 A1 | 10/2002 | Cole et al. |
| 2003/0055455 A1 | 3/2003 | Yang et al. |
| 2004/0215214 A1 | 10/2004 | Crews et al. |
| 2005/0021059 A1 | 1/2005 | Cole et al. |
| 2006/0271107 A1 | 11/2006 | Harrison et al. |
| 2007/0010834 A1 | 1/2007 | Sharkawy et al. |
| 2008/0114384 A1 | 5/2008 | Chang et al. |
| 2008/0200934 A1 | 8/2008 | Fox |
| 2009/0048618 A1 | 2/2009 | Harrison et al. |

FOREIGN PATENT DOCUMENTS

| | | |
|---|---|---|
| EP | 1493391 A1 | 1/2005 |
| FR | 2760627 A1 | 9/1998 |
| WO | 8100668 A1 | 3/1981 |
| WO | 2004105693 A2 | 12/2004 |
| WO | 2007016261 A2 | 2/2007 |
| WO | 2008061024 A2 | 5/2008 |
| WO | 2008150905 A1 | 12/2008 |
| WO | 2009029228 A2 | 3/2009 |

OTHER PUBLICATIONS

European Search Report for EP 10 25 0786, date of completion Aug. 11, 2010 (3 pages).

Japanese Official Action dated Mar. 24, 2014 issued in Japanese Appln. No. 2009-178905.

Canadian Office Action dated Jun. 3, 2015, issued in Canadian Application No. 2,671,070.

European Office Action dated Nov. 18, 2015, issued in EP Application No. 09251927.

* cited by examiner

MAGNETIC COMPRESSION ANASTOMOSIS DEVICE

CROSS-REFERENCE TO RELATED APPLICATIONS

This application is a continuation of U.S. patent application Ser. No. 14/175,353, filed Feb. 7, 2014, now U.S. Pat. No. 8,920,446, which is a continuation of U.S. patent application Ser. No. 12/486,846, filed Jun. 18, 2009, now U.S. Pat. No. 8,685,046, which claims priority from and benefit of Provisional Patent Application Ser. No. 61/086,340, filed Aug. 5, 2008,the disclosures of each of the above identified applications are hereby incorporated by reference in the entirety.

BACKGROUND

1. Technical Field

The present disclosure relates to a surgical device for treating hollow organs and, more particularly, to a surgical device suitable for performing circular anastomosis of hollow organs.

2. Discussion of Related Art

Anastomosis is the surgical joining of separate hollow organ sections. The site of the attachment is also sometimes called an anastomosis. Typically, an anastomosis procedure follows surgery in which a diseased or defective section of a hollow organ is removed and the remaining end sections are to be joined. Depending on the desired anastomosis procedure, the sections may be joined by end-to-end, end-to-side or side-to-side organ reconstruction methods. End-to-end anastomosis is generally performed using surgical staples.

The staples are usually left in the patient. In a circular stapled anastomosis procedure, the two ends of the organ sections are joined by means of a stapling instrument which drives a circular array of staples through the organ end sections and simultaneously cores and removes any tissue located interior of the driven circular array of staples to free a tubular passage.

In some applications of a circular anastomosis procedure, an anvil rod having an attached anvil head is mounted to the distal end of a surgical stapling instrument shaft prior to insertion of the instrument into the tissue to be anastomosed. However, in other applications, it is preferable to utilize a detachable anvil rod which may be mounted to the instrument subsequent to positioning of the instrument and the anvil assembly within respective tissue sections. In such instances, the stapling instrument and the anvil assembly are separately delivered to the operative site. Each tissue section is secured to a respective anvil or staple holding component by a purse string suture. The anvil assembly is mounted to the stapling instrument by inserting a mounting portion of the anvil rod within the distal end of the instrument so that a mounting mechanism within the instrument securely engages the rod.

FIG. 1 illustrates a surgical stapling instrument for performing circular anastomosis of hollow organs. Referring to FIG. 1, the stapling device 10 includes a proximal handle assembly 12, an elongated central body portion 14 including a curved elongated outer tube 14a, and a distal head portion 16. Handle assembly 12 includes a stationary handle 18, a firing lever 20, a rotatable approximation knob 22 and an indicator 24. Indicator 24 includes indicia, such as color coding or alpha-numeric labeling, to identify to a surgeon whether the device is approximated and is ready to be fired. Head portion 16 includes a staple holding component (cartridge) 31 and an anvil assembly 30 including an anvil rod 52 with attached anvil head 63. Opposed end portions of tissue to be stapled are clamped between the anvil head 63 and the staple holding component 31. The clamped tissue is stapled by driving one or more staples from the staple holding component 31 so that the ends of the staples pass through the tissue and are deformed by the anvil pockets of anvil head 63.

Methods and devices for forming anastomoses between hollow anatomical structures using magnetic force have been proposed. However, many of the proposed anastomotic couplings are simply too cumbersome and difficult to deliver or deploy.

It would be beneficial to provide a surgical device for performing circular anastomosis of hollow organs utilizing magnetic force that is easy to use and produces a reliable anastomosis, placing the hollow organs in flow communication.

SUMMARY

According to an exemplary embodiment of the present disclosure, an apparatus for joining organ wall portions of first and second hollow organs is disclosed. The apparatus includes first and second connectors, wherein the first and second connectors are magnetically attracted to one another. A device for delivering and deploying the first and second connectors to portions of the first and second hollow organs is also disclosed, wherein the device is configured and dimensioned to axially align the first and second connectors for performing circular anastomosis of the first and second hollow organs.

In one embodiment, the first connector has a proximal facing surface and the second connector has a distal facing surface, the proximal facing surface having a first polarity and the distal facing surface having a different polarity.

In one embodiment, the first connector has a proximal facing surface and the second connector has a distal facing surface, the proximal facing surface having regions of different polarity and the distal facing surface having regions of different polarity. The regions of different polarity can comprise alternating regions of different polarity. The distal facing surface of the second connector can have regions of different polarity.

In another aspect, an apparatus for joining organ wall portions of first and second hollow organs is disclosed. The apparatus comprises first and second connectors, the first connector having a proximal facing surface and the second connector having a distal facing surface. The proximal facing surface of the first connector has regions of different polarity and the first and second connectors are magnetically attracted to one another. In one embodiment the distal facing surface of the second connector has regions of different polarity. In one embodiment, the first and second connectors are substantially ring-shaped. In one embodiment the distal facing surface and proximal facing surface comprise alternating regions of different polarity such that on the proximal facing surface there are at least two regions of a first polarity and at least one region of a second polarity and on the distal facing surface there are at least two regions of the second polarity and at least one region of the first polarity.

In another aspect of the present disclosure, an apparatus for joining organ wall portions of first and second hollow organs includes a first connector capable of producing a magnetic field, a second connector capable of producing a magnetic field, and a device for delivering and deploying the first and second connectors to end portions of the first and second hollow organs. The device is configured and dimensioned to axially align the first and second connectors for forming an anastomosis that places the first and second hollow organs in flow communication. The device includes: a handle portion; a neck portion supported on a distal end of the handle portion, wherein the neck portion is configured to releasably house the second connector; and a head portion including a rod, the rod extending axially outward from a proximal end of the head portion and configured to be detachably mountable to a distal end of the neck portion, wherein the first connector is detachably affixed to the head portion.

BRIEF DESCRIPTION OF THE DRAWINGS

Objects and features of the presently disclosed magnetic compression anastomosis device will become apparent to those of ordinary skill in the art when descriptions of various embodiments thereof are read with reference to the accompanying drawings, of which.

DESCRIPTION OF EXEMPLARY EMBODIMENTS

Figure 1:
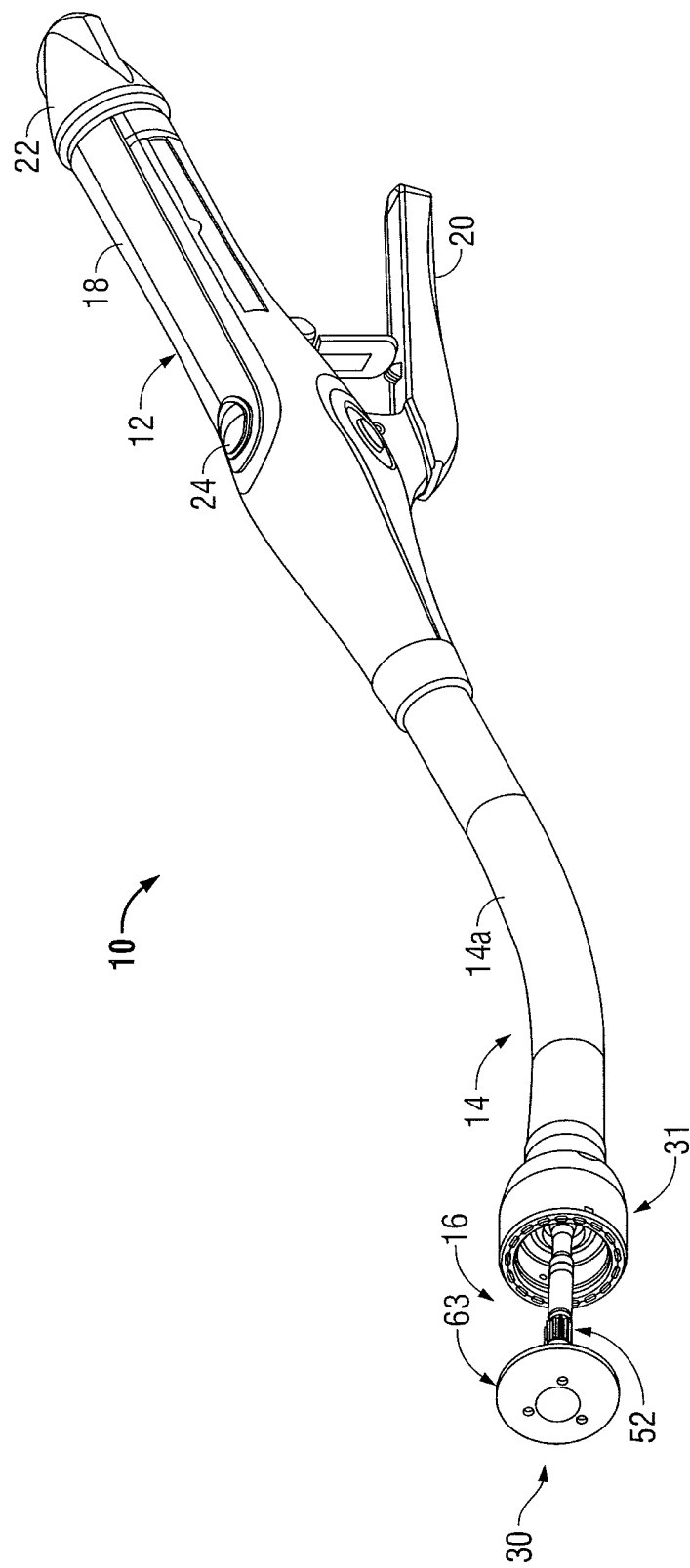
FIG. 1 is a top side perspective view of a prior art surgical stapling device in the unapproximated position.

Hereinafter, exemplary embodiments of the presently disclosed magnetic compression anastomosis device will be described with reference to the accompanying drawings. Like reference numerals may refer to similar or identical elements throughout the description of the figures. As used herein, the phrase "magnetic material" refers to any material capable of producing a magnetic field or any material that reacts to or is affected by a magnetic field.

In various exemplary embodiments, the presently disclosed magnetic compression anastomosis device includes first and second connectors, which are magnetically attracted to one another, and a delivery and deployment device configured and dimensioned to axially align the first and second connectors to facilitate the formation of an anastomosis between the two end portions of the organ sections to be joined.

Figure 2:
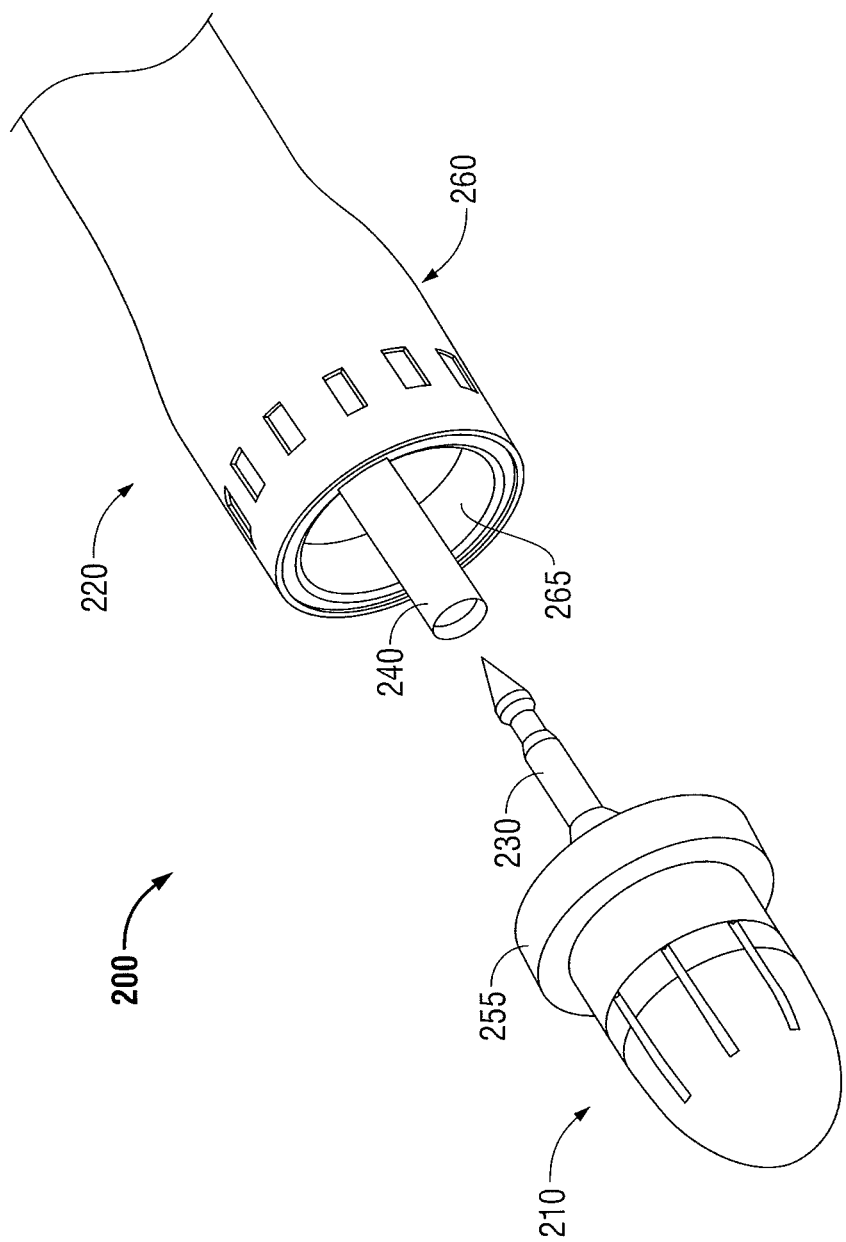
FIG. 2 is a perspective view of a magnetic compression anastomosis device, according to an exemplary embodiment of the present disclosure.
Figure 2A:
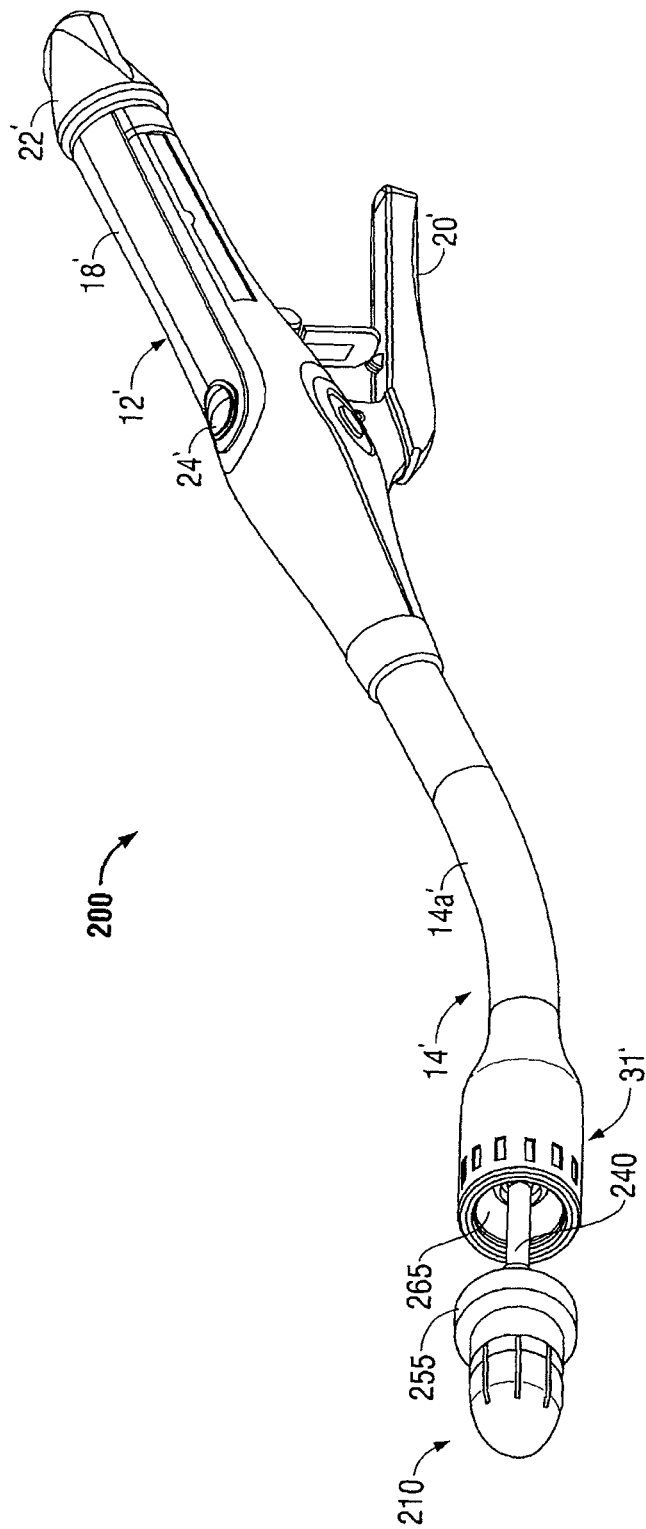
FIG. 2A is a perspective view of the anastomosis instrument for applying the magnetic compression anastomosis device.
Figure 3:
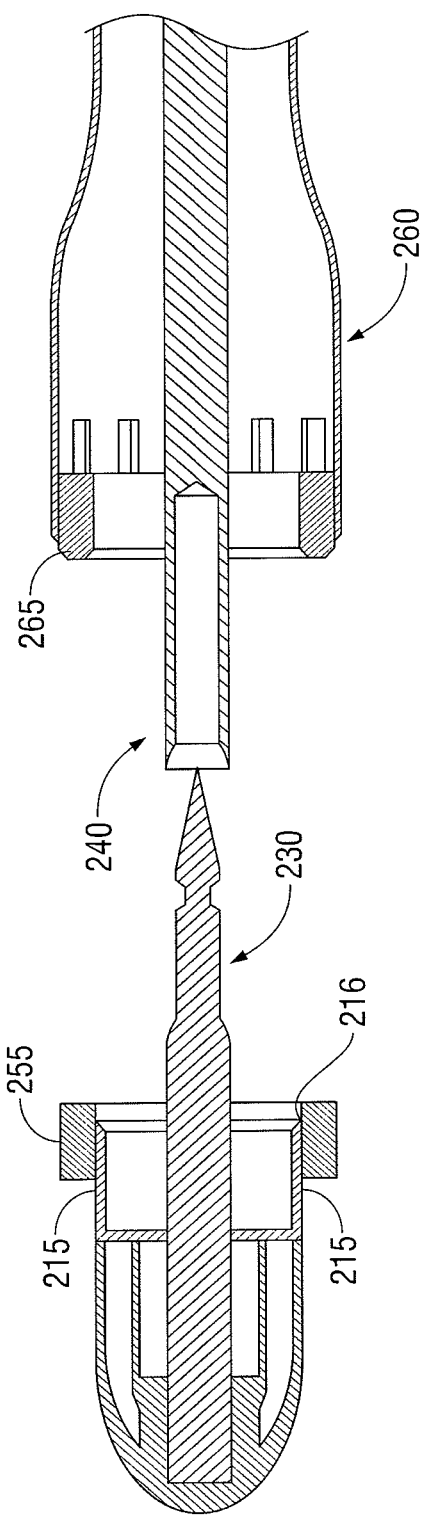
FIG. 3 is a cross-sectional view of the magnetic compression anastomosis device illustrated in FIG. 2.

FIGS. 2 and 3 illustrate a magnetic compression anastomosis device according to an exemplary embodiment. The magnetic compression anastomosis device 200 includes a neck portion 220 of magnetic holding component 31' extending from an elongated central body portion 14' (having a curved elongated outer tube 14a' shown in FIG. 2A), which is supported on an end of a handle assembly 12', a head portion 210, a first connector 255 detachably affixed to the head portion 210, and a second connector 265 releasably housed in the neck portion 220. In an exemplary embodiment of the presently disclosed magnetic compression anastomosis device, the first connector 255 is substantially the same as the first anastomotic connector 401 shown in FIG. 4A and the second connector 265 is substantially the same as the second anastomotic connector 402 shown in FIG. 4B.

Neck portion 220 includes an actuator or center rod 240 and a sleeve portion 260 at the distal end of the neck portion. The sleeve portion 260 releasably houses the second connector 265. The actuator shaft 240 is movable in relation to the sleeve portion 260 between a first retracted position and a second extended position by for example a rotation knob 22' (FIG. 2A). When the actuator 240 is in the second position, the head portion 210 is engageable and disengageable therefrom. Moving the actuator 240 to the first position (also referred to herein as "approximated position") approximates the two portions and prevents disengagement of the head portion 210 from the actuator 240. This can be achieved in various ways such as by providing spring structure (not shown) associated with the actuator 240 which engages the rod 230 and its movement is inhibited when the actuator 240 is retracted within neck 220. An example of such structure is disclosed in U.S. Pat. No. 7,303,106, the entire contents of which are incorporated by reference herein. The handle portion (not shown) may include an indicator 24' to provide an indication to a surgeon that the head portion 210 has been unapproximated a distance sufficient to allow removal of the head portion 210 from the actuator 240 or, alternatively, that any further unapproximation of the head portion 210 will move the head portion 210 to a position in which the head portion 210 can be disengaged from actuator 240. An example of an indicator which can be utilized is the indicator of U.S. Patent No. 7,303,106, incorporated herein in its entirety by reference. Sleeve portion 260 defines a sleeve body having a retaining portion defining a retaining body having a longitudinal throughbore dimensioned to slidably receive the second connector 265 therein.

Head portion 210 includes a knife 215 and a rod 230 extending from a proximal portion. Rod 230 extends axially outward from an end of the head portion 210 and includes a proximal end portion which is received within and engages a mounting mechanism (not shown) within the actuator 240 at a distal portion of the neck portion 220. The proximal end portion of the rod 230 may include a generally conical shaped mounting portion that is advantageously dimensioned to facilitate entry within the actuator 240 and which further enables manipulation of rod 230 through body tissue. It is to be understood that the proximal end portion of the rod 230 may include a number of portions having various shapes and dimensions. It is also contemplated that alternatively knife 215 can be provided in neck portion 220.

Figure 7A:
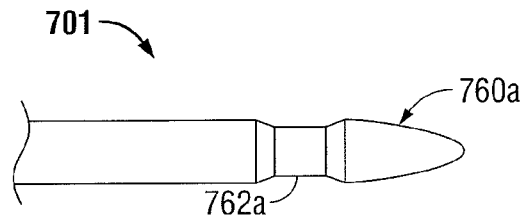
FIG. 7A is a perspective view of a rod of a head portion of a magnetic compression anastomosis device, according to one embodiment of the present disclosure.
Figure 7B:
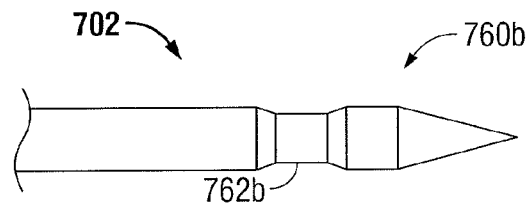
FIG. 7B is a perspective view of an alternate embodiment of a rod of a head portion of a magnetic compression anastomosis device.
Figure 7C:
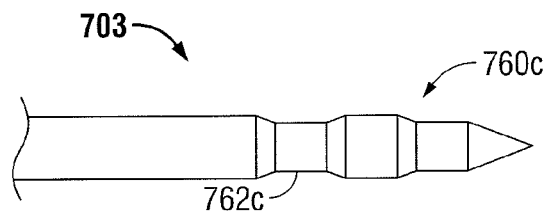
FIG. 7C is a perspective view of another alternate embodiment of a rod of a head portion of a magnetic compression anastomosis device.

FIGS. 7A, 7B and 7C illustrate by way of example various configurations of rods suitable for engaging a mounting mechanism (not shown) within the actuator 240 of the neck portion 220 of the magnetic compression anastomosis device 200. Rods 701, 702 and 703 shown in FIGS. 7A, 7B and 7C, respectively, include generally conical shaped mounting portions 760a, 760b and 760c, respectively. Each of the rods 701, 702 and 703 also includes an annular recess 762a, 762b and 762c, respectively, which is correspondingly configured to be engaged by the mounting mechanism (such as flexible spring arms) within the actuator 240. For example, the spring arms can engage the recess and when pulled within the sleeve portion 260 are blocked from outward movement to thereby prevent release of the respective rod 701, 702 or 703.

FIGS. 4A, 4B, 5A and 5B illustrate anastomotic connectors according to various embodiments of the present disclosure. Each of the anastomotic connectors shown in FIGS. 4A, 4B, 5A and 5B has a substantially annular ring shape having a top surface, an inner diameter surface adjacent to the top surface, an outer diameter surface adjacent to the top surface, and a bottom surface. It is to be understood that the shape and size of the anastomotic connectors may be varied from the exemplary configurations depicted in FIGS. 4A, 4B, 5A and 5B. The terms top and bottom surfaces are used for convenience and reflect the orientation of the connectors of FIGS. 4A and 4B.

Figure 4A:
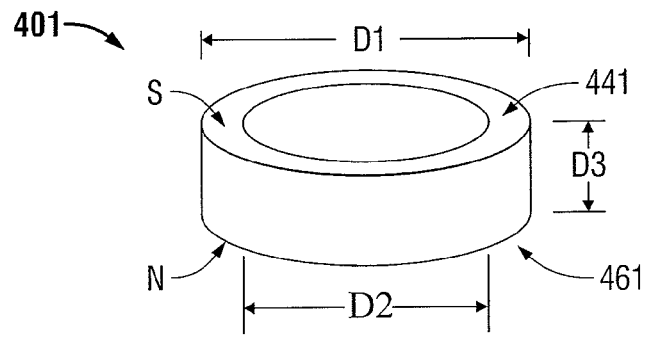
FIG. 4A is a perspective view of an anastomotic connector, according to an exemplary embodiment of the present disclosure.

The anastomotic connectors shown in FIGS. 4A, 4B, 5A and 5B may each include one or more materials, such as for example, magnetic and nonmagnetic materials. Each anastomotic connector includes a first dimension "D1", a second dimension "D2" and a third dimension "D3", where D1 defines the outer diameter, D2 defines the inner diameter, and D3 defines the height (or thickness) of the connector, as shown in FIG. 4A. (Only one of the connectors is labeled with "D" dimensions for clarity). It is to be understood that anastomotic connectors according to various embodiments of the presently disclosed magnetic compression anastomosis device 200 may have any suitable dimensions D1, D2 and D3. The actual dimensions D1, D2 and D3 may depend on various factors, such as for example, the size of the hollow organ sections to be treated, the desired anastomosis procedure, and the materials used to form the anastomotic connectors.

Figure 4B:
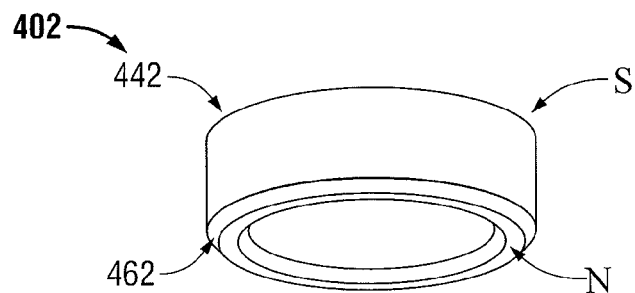
FIG. 4B is a perspective view of an anastomotic connector, according to an exemplary embodiment of the present disclosure.

Referring to FIGS. 4A and 4B, each of the first and second anastomotic connectors 401, 402 has its north pole indicated by the letter "N" and its south pole indicated by the letter "S". First and second anastomotic connectors 401, 402 are each preferably formed substantially entirely of a suitable magnetic material capable of producing a magnetic field. In another embodiment, at least one of the first anastomotic connector 401 or the second anastomotic connector 402 includes portions of at least one non-magnetic material. Examples of magnetic materials that may be used to form the first and second anastomotic connectors 401, 402 include, but are not limited to, NdFeB (Neodymium Iron Boron), AlNiCo (Aluminum Nickel Cobalt) SmCo (Samarium Cobalt), strontium ferrite and barium ferrite. In an alternate embodiment, one of the connectors would include material which produces a magnetic field and the other connector would be made of a material which reacts to the magnetic field, but does not necessarily produce a magnetic field, such as iron. It should be appreciated though that in the preferred embodiment both connectors include magnetic material which produces a magnetic field which would increase the attraction.

First anastomotic connector 401 has a generally annular body having a top surface 441, which corresponds to its south pole S, and a bottom surface 461, which corresponds to its north pole N. The top and bottom surfaces 441, 461 are generally flat and spaced apart by a suitable distance D3. Although the top and bottom surfaces 441, 461 of the first anastomotic connector 401 shown in FIG. 4A are generally flat, it is to be understood that the top and bottom surfaces of anastomotic connectors according to various embodiments may be non-flat, e.g. curved, or may include a combination of flat, sloped or curved portions.

Second anastomotic connector 402 illustrated in FIG. 4B has a generally annular body having a top surface 442, which corresponds to its south pole S, and a bottom surface 462, which corresponds to its North pole N. Second anastomotic connector 402 has a shape similar to that of the first anastomotic connector 401 shown in FIG. 4A, except the bottom surface 462 of the second connector 402 has an anvil-like shape that includes flat, sloped and curved portions. Other shapes are also contemplated.

Figure 8:
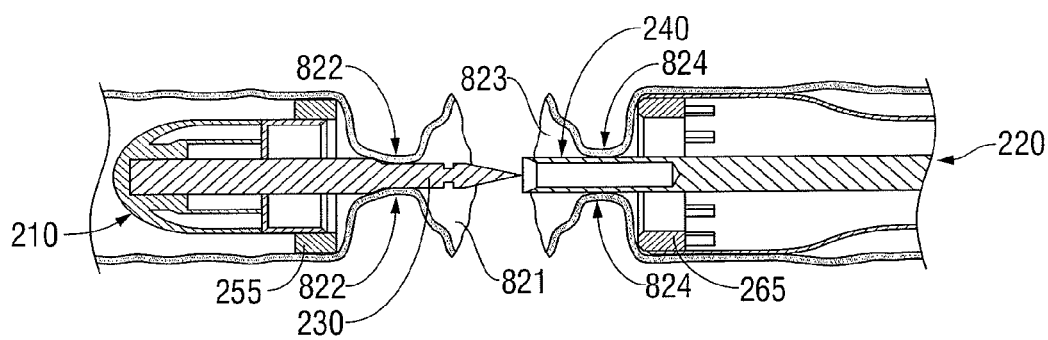
FIG. 8 is a cross-sectional view showing the head and neck portions of the magnetic compression anastomosis device illustrated in FIGS. 2 and 3 separately delivered to two organ end sections, according to an exemplary embodiment of the present disclosure.
Figure 9:
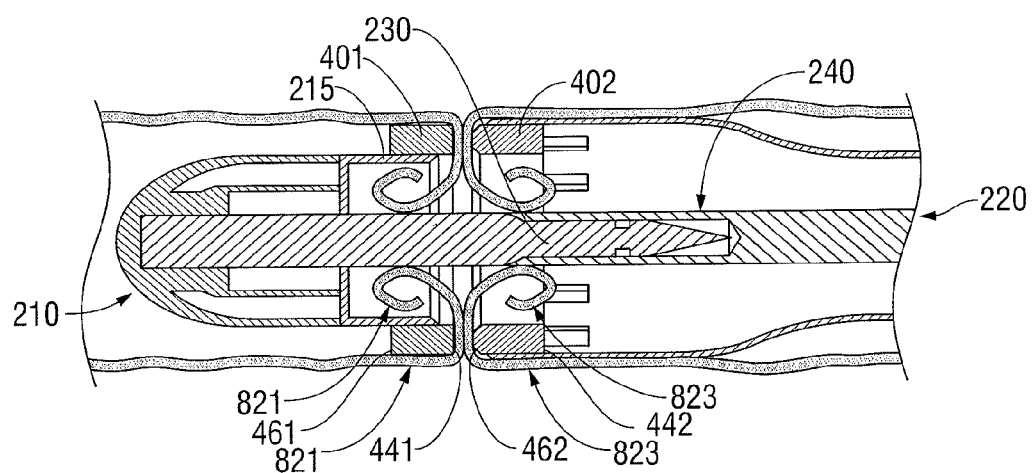
FIGS. 9-11 are cross-sectional views of the magnetic compression anastomosis device illustrated in FIGS. 2 and 3 showing the deployment of axially-aligned anastomotic connectors, according to exemplary embodiments of the present disclosure.
Figure 10:
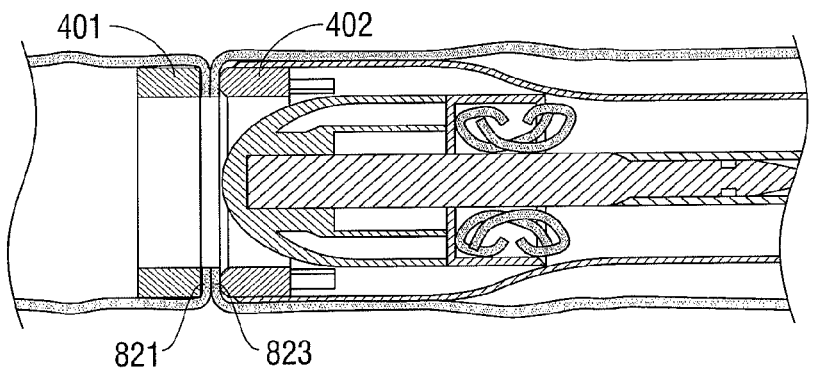
Figure 11:
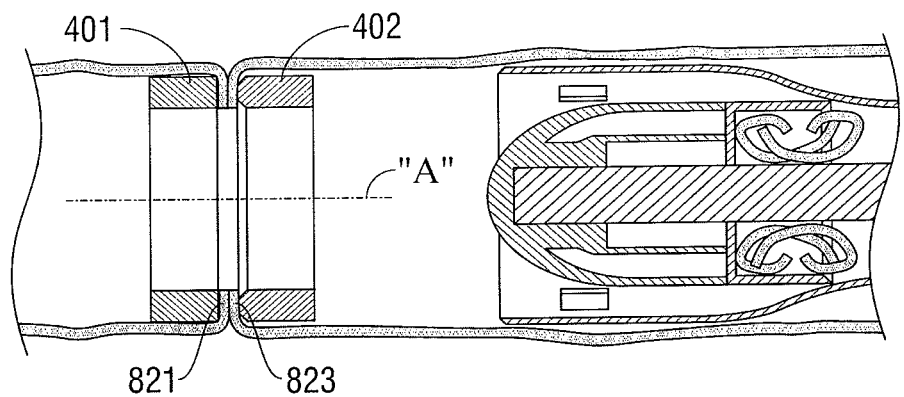

In a desired anastomosis procedure, the surgeon utilizes the magnetic compression anastomosis device 200 of FIG. 2 to deliver the first and second connectors 401, 402 (designated as 255, 265 in FIGS. 2 and 3) to the respective end portions of the organ sections to be joined. In the interests of clarity and simplicity, the first and second connectors 255, 265 are hereinafter referred to as the first and second anastomotic connectors 401, 402. However, it is to be understood that various configurations of anastomotic connectors can be used for the first and second connectors, such as the exemplary anastomotic connectors shown in FIGS. 5A and 5B and FIGS. 6A through 6D. Procedures for the delivery of the head and neck portions 210, 220 carrying the first and second anastomotic connectors 401, 402 to the end portions of the hollow organs to be joined are described later in this disclosure with reference to FIG. 8. After the delivery of the head and neck portions 210, 220, the surgeon uses the magnetic compression anastomosis device 200 to deploy axially-aligned first and second anastomotic connectors 401, 402, as shown in FIGS. 9-11. As shown, the top surface (south pole) 441 of connector 401 (255) faces proximally and the bottom surface 462 (north pole) of connector 402 (265) faces distally. The magnetic attraction between opposite poles of the axially-aligned first and second anastomotic connectors 401, 402 facilitates the formation of a reliable anastomosis. For example, in one instance, the magnetic attraction between the top surface 441 of the first anastomotic connector 401 and the bottom surface 462 of the second anastomotic connector 402 maintains the two end portions of the organ sections in intimate contact with one another, forming a fluid-tight anastomosis.

In another embodiment (not shown), the first and second anastomotic connectors 401, 402 are arranged in the magnetic compression anastomosis device 200 for delivery and deployment such that the bottom surface 461 and top surface 462 of the first and second anastomotic connectors 401, 402, respectively, are oriented towards each other. That is, the bottom surface 461 of first connector 401 (255) faces proximally and the top surface 442 of connector 402 (265) faces distally. In this instance, after the first and second anastomotic connectors 401, 402 are deployed, the magnetic attraction between opposite poles of the surfaces 461, 442 maintain the two end portions of the organ sections in intimate contact with one another, forming a fluid-tight anastomosis.

Thus, a pair of anastomotic connectors according to various embodiments can be arranged in two orientations based on the magnetic polarities of the respective top and bottom surfaces. In instances where the respective top and/or bottom surfaces of a pair of anastomotic connectors have different configurations, the surgeon is provided an increased flexibility in performing a desired anastomosis procedure.

The amount of compression force exerted by the axially-aligned first and second anastomotic connectors 401, 402 on tissue of hollow organ wall portions to be joined will depend on various factors, including the magnetic materials used to form the first and second anastomotic connectors 401, 402, the specific dimensions D1, D2 and D3 of the first and second anastomotic connectors 401, 402, and thickness of tissue to be joined.

Figure 5A:
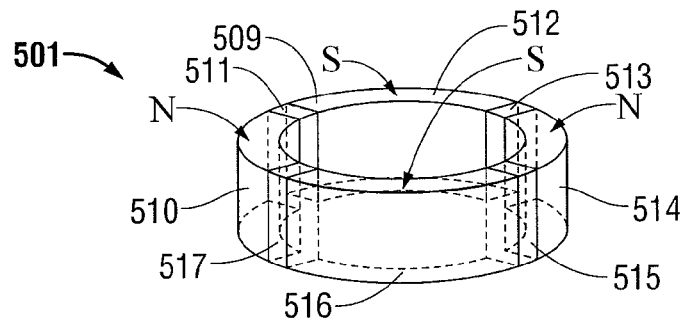
FIG. 5A is a perspective view of an anastomotic connector, according to an alternate embodiment of the present disclosure.
Figure 5B:
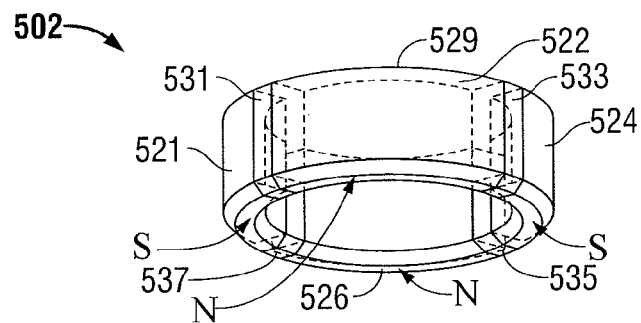
FIG. 5B is a perspective view of an anastomotic connector, according to an alternate embodiment of the present disclosure.

FIGS. 5A and 5B illustrate first and second anastomotic connectors, according to another exemplary embodiment of the present disclosure. Although the first and second anastomotic connectors 501, 502 are shaped similar to the first and second anastomotic connectors 401, 402 shown in FIGS. 4A and 4B, respectively, the first and second anastomotic connectors 501, 502 are annular four-pole configurations having four "N" and "S" magnetic poles. First and second anastomotic connectors 501, 502 include one or more materials capable of producing a magnetic field, such as for example, NdFeB, AlNiCo, SmCo, strontium ferrite, barium ferrite, or any combination thereof, and may include substantially rigid materials, such as for example, metal, synthetic or compound materials. Alternatively, one of the connectors 501, 502 can include one or more materials capable of producing a magnetic field and the other connector can include one or more materials reactive to or affected by a magnetic field, such as iron.

Referring to FIG. 5A, the first anastomotic connector 501 includes four first-type regions 510, 512, 514 and 516 and four second-type regions 511, 513, 515 and 517, collectively together forming an annular body. In an exemplary embodiment, the first-type regions 510, 512, 514 and 516 are magnetic regions (with the poles as indicated) and the second-type regions 511, 513, 515 and 517 are non-magnetic material regions. For example, in one instance, the non-magnetic material regions 511, 513, 515 and 517 are individually arranged between the magnetic regions 510, 512, 514 and 516 whereby the magnetic regions (of alternating polarity) are each separated from one another. Similarly, anastomotic connector 502 has four first-type regions 521, 522, 524, 526 and four second-type regions 531, 533, 535, 537, preferably magnetic and non-magnetic material, respectively, as described with respect to connector 501. Other arrangements of the north and south poles on the top surface are also contemplated to achieve the function of magnetic attraction of the rings. Alternatively, one of the connectors can have magnetic regions that produce a magnetic field and the other connector have magnetic regions that react to the magnetic field.

The device of FIGS. 2, 2A and 3, with the handle and approximation mechanisms similar to FIG. 1, can be used to apply the connectors 501, 502 to tissue. In use, after the delivery of the head and neck portions 210, 220, the surgeon uses the magnetic compression anastomosis device to deploy axially-aligned first and second anastomotic connectors 501, 502. The top surface 509 (as viewed in the orientation of FIG. 3A) of connector 501 faces proximally and the top surface 529 (as viewed in the orientation of FIG. 3A) of connector 502 faces distally. Rotation of approximation knob 22' moves the connectors into approximation as rod 24o is pulled proximally. The magnetic attraction can release the respective connectors from the head portion 210 and neck portion 220, or alternatively handle 20' can be pivoted relative to stationary handle 18' to advance a pusher (not shown) to advance the connector 265 from neck portion 220.

The magnetic attraction between opposite poles of the first and second anastomotic connectors 501, 502 facilitates the formation of a reliable anastomosis. That is, the magnetic attraction between the surfaces 509, 529 of the first and second anastomotic connectors 501, 502 maintains the two end portions of the organ sections in intimate contact with one another, forming a fluid-tight anastomosis as the magnetic attraction applies a clamping/holding force. The placement of alternating north and south poles on the facing surfaces minimizes rotation of the connectors with respect to one another.

The amount of compression force exerted by the first and second anastomotic connectors 501, 502 on the tissue of the hollow organ wall portions to be joined wills depend on various factors, including the materials used to form the magnetic regions, the relative sizes of the magnetic and non-magnetic regions, and thickness of tissue to be joined.

In an alternate embodiment, an outer portion, e.g. an outer ring portion, of one connector has a first polarity and an inner portion, e.g. an inner ring portion, has a different polarity. The inner and outer portions of different polarities can occupy various areas of the connector. The opposing connector would have inner and outer portions of opposite polarity or of reactive material. This is shown for example in the embodiment of FIG. 6A.

Figure 6A:
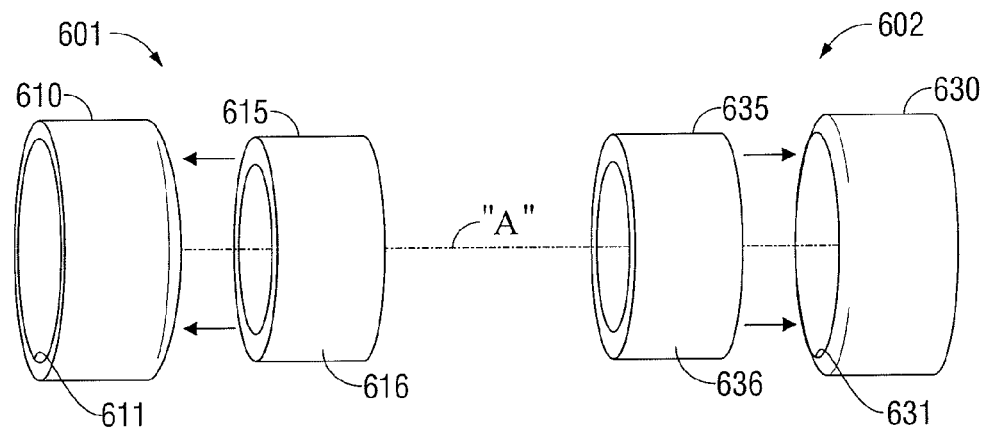
FIG. 6A is an exploded view illustrating two anastomotic connector assemblies having inner and outer connector members, according to another embodiment of the present disclosure.
Figure 6B:
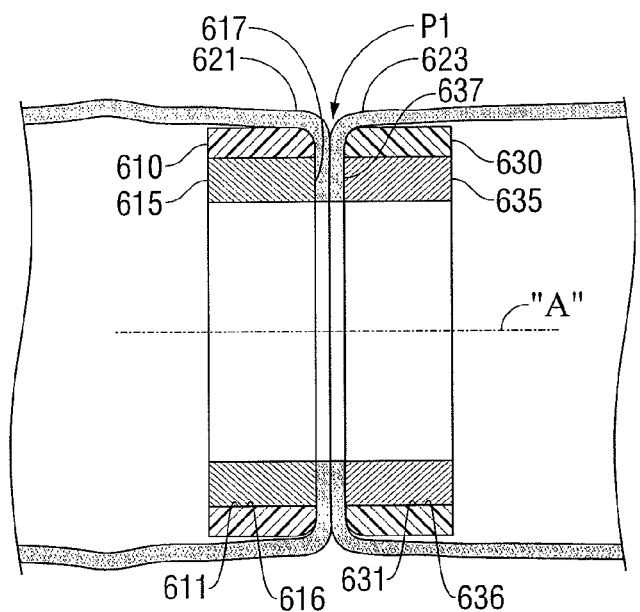
FIG. 6B is a cross-sectional view of organ wall portions of two hollow organs showing the axially-aligned anastomotic connector assemblies shown in FIG. 6A.

FIGS. 6A through 6D illustrate various embodiments of anastomotic connector assemblies having inner and outer connector members. Referring first to FIG. 6A, the first anastomotic connector assembly 601 includes an outer connector member 610 and an inner connector member 615, the outer connector member 610 having an annular body that includes an inner diameter wall 611 and the inner connector member 615 having an annular body that includes an outer diameter wall 616. Similarly, the second anastomotic connector assembly 602 includes an outer connector member 630 and an inner connector member 635, the outer connector member 630 having an annular body that includes an inner diameter wall 631 and the inner connector member 635 having an annular body that includes an outer diameter wall 636. The outer diameter walls 616, 636 of the inner connector members 615, 635 are dimensioned to fit within the inner diameter walls 611, 631 of the outer connector members 610, 630, respectively, as shown in FIG. 6B.

In one embodiment, the inner connector members 615, 635 and the outer connector members 610, 630 each include one or more magnetic materials. For example, the opposing surfaces of the inner members and the opposing surfaces of the outer members can have opposite poles, arranged in a continuous or in a spaced pattern (e.g. alternating pattern) on the individual surface. In another embodiment, the inner connector members 615, 635 each include one or more magnetic materials, and at least one of the outer connector members 610, 630 includes one or more non-magnetic materials. In yet another embodiment, the outer connector members 610, 630 each include one or more magnetic materials, and at least one of the inner connector members 615, 635 includes one or more non-magnetic materials. The poles in these embodiments can be arranged on opposite surfaces of the assemblies 601, 602 (e.g. continuous) as in the embodiment of FIG. 4A or arranged in spaced, e.g. alternating, fashion as in the embodiment of FIG. 5A, or arranged in other patterns.

First anastomotic connector assembly 601 can be constructed by placing the inner connector member 615 within the inner diameter wall of the outer connector member 610, as indicated by the leftward arrows in FIG. 6A. The outer diameter wall 616 of the inner connector member 615 may include a number of attachment flanges and/or recesses (not shown) which may be configured to engage with correspondingly configured recesses and/or attachment flanges formed on the inner diameter wall 611 of the outer connector member 610, for example, to facilitate the positioning or securing of the inner and outer connector members 615, 610. Such structures can also be used to attach inner and outer connector members 635, 630.

In one embodiment, the inner and outer connector members 615, 610 are permanently bonded together, for example, using a suitable adhesive or other bonding agent. In another embodiment, the inner and outer connector members 615, 610 are releasably attached to one another. For example, the inner and outer connector members 615, 610 may be releasably attached using magnetic attraction, releasable adhesives, protrusions and/or recesses, or any combination thereof. Similar methods can be used to connect inner and outer connector members 635, 630. First and second anastomotic connector assemblies 601, 602 shown in FIGS. 6A and 6B can be constructed in a like fashion, and the two components of connector assembly 602 can be attached in any of the ways as described for connector assembly 601, and further description of attachment of the components of the second anastomotic connector assembly 602 is omitted in the interests of brevity.

FIG. 6B illustrates organ wall portions of two hollow organs showing the axially-aligned anastomotic connector assemblies 601, 602 of FIG. 6A. At the stage of an anastomosis procedure depicted in FIG. 6B, the anastomotic connector assemblies have been delivered and deployed and are shown axially-aligned along the centerline "A". Referring to FIG. 6B, the magnetic attraction between opposite poles on surfaces 617, 637 of the inner connector members 615, 635 of the axially-aligned anastomotic connector assemblies 601, 602 maintains the tissue 621, 623 in intimate contact with one another. Additionally, opposite poles (of opposite polarity of the inner connector member positioned therein) could be provided on the facing surfaces of the outer connector members 610, 630, to further maintain the tissue in intimate contact.

Figure 6C:
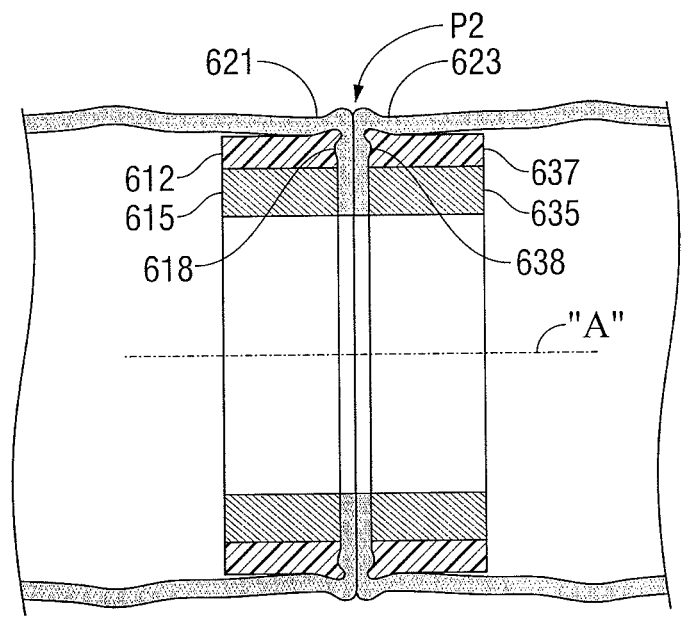
FIG. 6C is a cross-sectional view of organ wall portions of two hollow organs showing two axially-aligned anastomotic connector assemblies, according to another alternate embodiment of the present disclosure.
Figure 6D:
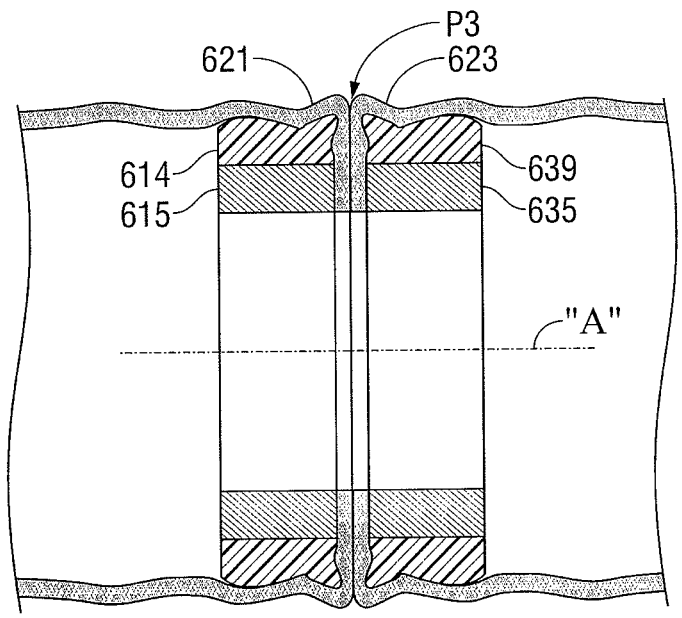
FIG. 6D is a cross-sectional view of organ wall portions of two hollow organs showing two axially-aligned anastomotic connector assemblies, according to yet another alternate embodiment of the present disclosure.

The anastomotic connector assemblies illustrated in FIGS. 6C and 6D are similar to the anastomotic connector assemblies shown in FIG. 6B, except the outer connector members of the anastomotic connector assemblies shown axially-aligned along the centerline "A" in FIGS. 6C and 6D are adapted to provide an increased tissue-to-tissue contact area at the anastomosis site. An increased tissue-to-tissue contact area may increase strength, stability and tissue resiliency at the anastomosis site, which may reduce the risk of patients suffering an anastomotic leak.

Referring to FIG. 6C, the outer diameter wall of each of the outer connector members 612, 637 includes a protrusion 618', 638' configured to produce an increased surface area of tissue 621, 623 maintained in intimate contact, as compared to the outer connector members 610, 630 shown in FIG. 6B. The protrusion on the outer connector members 612, 637 results in an increased contact area between the tissue 621, 623 of the organ wall portions to be joined at the point "P2" in FIG. 6C, as compared to that at point "P1" in FIG. 6B, because the protrusion is advantageously shaped to reduce the angle of separation between the tissue 621, 623 at the point "P2", as compared to point "P1", when the anastomotic connector assemblies are axially-aligned.

Another embodiment of outer connector members adapted to provide an increased tissue-to-tissue contact area at the anastomosis site when the anastomotic connector assemblies are axially-aligned is shown in FIG. 6D. Referring to FIG. 6D, the protrusion on the outer connector members 614, 639 is advantageously shaped to reduce the angle of separation between the tissue 621, 623 of the organ wall portions to be joined at the point "P3", as compared to that at the point "P1" in FIG. 6B, which results in an increased contact area between the tissue 621, 623 at the point "P3". Also, the outer surface of the connector members 614 and 639 has curves as shown. It is to be understood that the shape and size of the outer connector members may be varied from the exemplary configurations depicted in FIGS. 6C and 6D.

In an anastomosis procedure, the surgeon separately delivers the head and neck portions 210, 220 of the magnetic compression anastomosis device 200 into the end portions of first and second hollow organs. FIG. 8 illustrates the head and neck portions 210, 220 separately delivered to first and second hollow organs according to an exemplary embodiment. Referring to FIG. 8, after the insertion of the head portion 210 into the first hollow organ, a purse string suture 822 is used to pull the organ wall portion 821 towards the rod 230. After the insertion of the neck portion 220 of the instrument 200 into the second hollow organ, a purse string suture 824 is used to pull the organ wall portion 823 towards the center rod 824 (similar to the center rod 240 of FIG. 2A). Although purse string sutures 822, 824 are used in the embodiment illustrated in FIG. 8, it is to be understood that any suitable means of securing the organ wall portions 821, 823 to the rod 230 and rod 240, respectively, may be utilized. The rods are then mated as described above and the head and neck portions 210, 220 approximated as described above (e.g. by rotation knob retracting the center rod), followed by deployment of the connectors (e.g. by magnetic attraction releasing the connectors as they move a sufficient distance toward each other or by a pusher ejecting the connector in the neck portion 22). The various embodiments of the connectors described herein can be placed in the same manner.

FIGS. 9-11 are cross-sectional views of the magnetic compression anastomosis device illustrated in FIGS. 2 and 3 showing deployment of the anastomotic connectors, according to an exemplary embodiment of the present disclosure. Referring to FIG. 9, the head portion 210 is mounted to the neck portion 220 by inserting a mounting portion of the rod 230 within the actuator (center rod) 240 so that a mounting mechanism within the actuator 240 securely engages the rod 230. To "fire" the magnetic compression anastomosis device 200, the actuator 240, including the attached head portion 210, is retracted into the neck portion 220 (by use of an approximation knob 22' similar to knob 22 of FIG. 1 by way of example), pulling in the two organ wall portions 821, 823 into close approximation, whereupon magnetic attraction between the axially-aligned anastomotic connectors 401, 402 takes hold, releasing them from the instrument due to the magnetic force and thereby providing a compression force that maintains the organ wall portions 821, 823 in intimate contact. Alternatively, as described above, a pusher can be utilized, actuated by handle 20'.

Referring to FIG. 10, as the head portion 210 is retracted into the neck portion 220, an annular knife 215 (shown in FIG. 3) is pulled through tissue. (Note the edge 216 of the knife-can be shielded by the connector 255 as shown in FIG. 3). Alternatively, the annular knife could be positioned in the neck portion 220 and advanced by a separate knife advancing mechanism (not shown) to core tissue within the hollow organ containing the purse strings 822, 824 to create a tubular passage within the organ. The knife advancing mechanism can be actuated for example by handle 20' of instrument 200. Referring to FIG. 11, the first and second anastomotic connectors 401, 402 are shown axially aligned along the centerline "A", producing a reliable anastomosis that places the first and second hollow organs in flow communication. The head and neck portions 210, 220 of the magnetic compression anastomosis device 200 are removed from the patient's body. The magnetic compression anastomosis device 200 could be easily reloaded with connecting members, if desired, and fired several times on the same patient.

Figure 12:
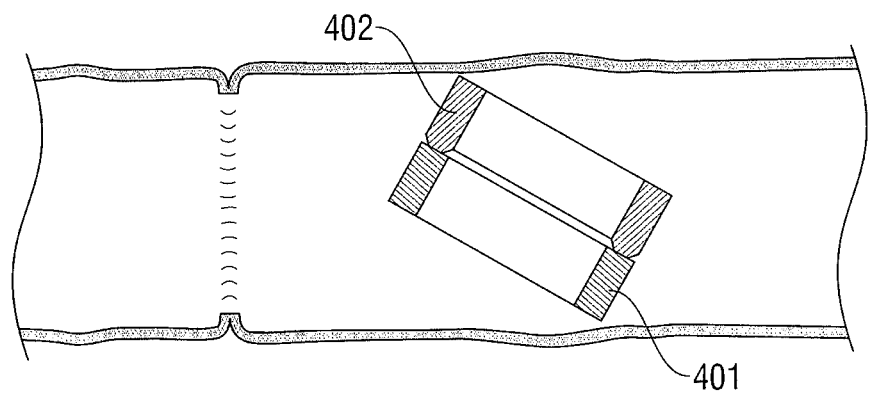
FIG. 12 is a cross-sectional view of organ wall portions of two hollow organs showing the anastomotic connectors of FIG. 11 falling free as a result of tissue necrosis, according to an exemplary embodiment of the present disclosure.

With time, such as several days, the tissue under a ring of modest pressure begins to heal. The tissue under severe pressure begins to necrose and die, allowing the first and second anastomotic connectors 401, 402 to fall free and naturally pass out of the body, as shown in FIG. 12. Accordingly, in a preferred embodiment, no foreign materials are left permanently in the patient's body.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing exemplary embodiments may be made without departing from the scope of the disclosure.

What is claimed is:

1. An apparatus for joining organ walls of first and second hollow organs, comprising:
   a first connector;
   a second connector defining a cavity, the first and second connectors magnetically attracted to one another; and
   a device for delivering and deploying the first and second connectors to the first and second hollow organs, the device including a first portion and a second portion, the second portion sized to pass through the first and second connectors, the first portion releasably housing the second connector at a distal end thereof and the second portion releasably affixed to the first connector, the second portion including a cutting edge facing the first portion and configured to pass through the cavity of the second connector, wherein the first portion includes an actuator that is releasably engageable with the second portion and is moveable between a first position in which disengagement of the second portion from the actuator is allowed and a second position in which disengagement of the second portion from the actuator is prevented.

2. The apparatus of claim 1, wherein at least one of the first and second connectors produces a magnetic field.

3. The apparatus of claim 1, wherein each of the first and second connectors produces a magnetic field.

4. The apparatus of claim 1, wherein the cutting edge is configured to core tissue within the cavity.

5. The apparatus of claim 1, wherein the cutting edge is disposed on an outer dimension of the second portion.

6. The apparatus of claim 5, wherein the cutting edge is annular.

7. The apparatus of claim 5, wherein the cutting edge defines a diameter less than a diameter defined by the cavity.

8. The apparatus of claim 1, wherein the second portion includes a proximally extending rod received by the first portion.

9. The apparatus of claim 1, wherein the second portion includes a rod, the rod of the second portion being releasably engagable with the actuator.

10. The apparatus of claim 1, wherein the second portion includes a rod, the rod of the second portion being slidably engagable with the actuator such that as the device is actuated, the rod approximates the first and second portions together to bring the first and second connectors into close approximation with one another, wherein the magnetic attraction between the first and second connectors applies a compressive force to tissue captured therebetween.

11. The apparatus of claim 1, wherein the first and second connectors define annular bodies.

12. The apparatus of claim 1, wherein at least one of the first and second connectors includes a protrusion on a surface facing the other one of the first and second connectors.

13. The apparatus of claim 1, wherein at least one of the first and second connectors includes an inner connector member and an outer connector member.

* * * * *